United States Patent
Rykhus et al.

(10) Patent No.: US 9,795,733 B2
(45) Date of Patent: Oct. 24, 2017

(54) METHOD AND APPARATUS FOR COMPENSATING FOR INJECTION MEDIA VISCOSITY IN A PRESSURIZED DRUG INJECTION SYSTEM

(71) Applicants: Robert L. Rykhus, Edina, MN (US); Justin M. Crank, Maple Grove, MN (US)

(72) Inventors: Robert L. Rykhus, Edina, MN (US); Justin M. Crank, Maple Grove, MN (US)

(73) Assignee: Astora Women's Health Holdings, LLC, Minnetonka, MN (US)

(*) Notice: Subject to any disclaimer, the term of this patent is extended or adjusted under 35 U.S.C. 154(b) by 0 days.

(21) Appl. No.: 15/233,040

(22) Filed: Aug. 10, 2016

(65) Prior Publication Data
US 2016/0367749 A1 Dec. 22, 2016

Related U.S. Application Data

(62) Division of application No. 13/142,793, filed as application No. PCT/US2009/006383 on Dec. 4, 2009, now Pat. No. 9,421,326.

(60) Provisional application No. 61/141,153, filed on Dec. 29, 2008.

(51) Int. Cl.
*A61M 5/145* (2006.01)
*A61M 31/00* (2006.01)
*A61M 37/00* (2006.01)

(52) U.S. Cl.
CPC .......... *A61M 5/1452* (2013.01); *A61M 31/00* (2013.01); *A61M 37/00* (2013.01); *A61M 2205/3341* (2013.01); *A61M 2205/70* (2013.01)

(58) Field of Classification Search
CPC ........ A61M 5/1452; A61M 2205/3341; A61M 2205/70
See application file for complete search history.

(56) References Cited

U.S. PATENT DOCUMENTS

| | | | |
|---|---|---|---|
| 4,093,108 A | 6/1978 | Hein et al. |
| 4,130,119 A | 12/1978 | Sessions et al. |
| 4,742,817 A | 5/1988 | Kawashima et al. |
| 4,946,442 A | 8/1990 | Sanagi |
| 5,007,897 A | 4/1991 | Kalb et al. |
| 5,116,313 A | 5/1992 | McGregor |
| 5,178,603 A | 1/1993 | Prince |

(Continued)

FOREIGN PATENT DOCUMENTS

| | | |
|---|---|---|
| DE | 196 17 949 A1 | 10/1997 |
| DE | 196 50 115 C1 | 7/1998 |
| EP | 0 764 449 A2 | 3/1997 |

*Primary Examiner* — Emily Schmidt
*Assistant Examiner* — Lauren M Peng
(74) *Attorney, Agent, or Firm* — Kagan Binder, PLLC (57) ABSTRACT

A needleless injection system is provided to deliver therapeutic fluids to an internal treatment site in a patient, where the system is pressurized and is capable of compensating for differences in injection media viscosity and mechanical system characteristics. In one aspect, a needleless therapeutic fluid injection system is provided that includes modular, interchangeable components. In particular, the system includes a console that generally includes the electronic and/or hydraulic control components for the system, an injection chamber, and a shaft or catheter tube.

11 Claims, 4 Drawing Sheets

(56) References Cited

U.S. PATENT DOCUMENTS

| | | |
|---|---|---|
| 5,261,889 A | 11/1993 | Laine et al. |
| 5,336,178 A | 8/1994 | Kaplan et al. |
| 5,693,016 A | 12/1997 | Gumaste et al. |
| 5,720,721 A | 2/1998 | Dumas et al. |
| 5,840,062 A | 11/1998 | Gumaste et al. |
| 6,203,533 B1 | 3/2001 | Ouchi |
| 6,210,378 B1 | 4/2001 | Ouchi |
| 6,238,336 B1 | 5/2001 | Ouchi |
| 6,280,413 B1 | 8/2001 | Clark et al. |
| 6,400,980 B1 | 6/2002 | Lemelson |
| 6,520,928 B1 * | 2/2003 | Junior ............... A61M 5/14546 604/152 |
| 6,537,205 B1 | 3/2003 | Smith |
| 6,547,767 B1 | 4/2003 | Moein |
| 6,641,553 B1 | 11/2003 | Chee et al. |
| 6,905,475 B2 | 6/2005 | Hauschild et al. |
| 7,749,156 B2 | 7/2010 | Ouchi |
| 2003/0018304 A1 | 1/2003 | Sage, Jr. |
| 2003/0163111 A1 | 8/2003 | Daellenbach |
| 2004/0030320 A1 | 2/2004 | Chee et al. |
| 2004/0162528 A1 | 8/2004 | Horvath et al. |
| 2005/0192530 A1 | 9/2005 | Castellano |
| 2005/0228225 A1 | 10/2005 | Hauschild et al. |
| 2006/0129125 A1 | 6/2006 | Copa et al. |
| 2006/0213249 A1 | 9/2006 | Uram et al. |
| 2007/0167921 A1 | 7/2007 | Burren et al. |
| 2007/0191758 A1 * | 8/2007 | Hunter .................. A61B 17/20 604/22 |
| 2007/0225554 A1 | 9/2007 | Maseda et al. |
| 2008/0114203 A1 | 5/2008 | Crank |
| 2008/0119784 A1 | 5/2008 | Roychowdhury et al. |
| 2009/0093774 A1 * | 4/2009 | Wang .................. A61M 5/142 604/247 |
| 2009/0125014 A1 | 5/2009 | Bouthillier et al. |

\* cited by examiner

METHOD AND APPARATUS FOR COMPENSATING FOR INJECTION MEDIA VISCOSITY IN A PRESSURIZED DRUG INJECTION SYSTEM

CROSS-REFERENCE TO RELATED APPLICATION

This application is a divisional application of U.S. patent application Ser. No. 13/142,793, filed Jan. 29, 2011, which claims priority to and the benefit of International Application No. PCT/US2009/006383, filed on Dec. 4, 2009, which in turn claims priority under 35U.S.C. §119(e) to U.S. Provisional Application No. 61/141,153 (Rykus), filed Dec. 29, 2008, titled "Method and Apparatus for Compensating for Injection Media Viscosity in a Pressurized Drug Injection System," the entire contents of which are incorporated herein by reference in their entireties.

TECHNICAL FIELD

The present invention relates generally to the delivery of therapeutic fluids to a treatment site within a patient. More specifically, the invention relates to methods and devices for treating tissue within the human body using a pressurized injection system that delivers therapeutic fluids to a desired location, such as the urinary tract of a patient.

BACKGROUND

A wide variety of medical treatments utilize the delivery and introduction of therapeutic compositions to a treatment location in a patient. In home or outpatient settings, the delivery methods used can include procedures such as oral delivery or inhalants, while in clinical or hospital types of settings, a therapeutic fluid is often injected using a needle-based system. In more complicated methods, a fluid can be delivered surgically through a tubular device, such as a catheter or endoscope, and in some cases, the surgical method can involve minimally invasive procedures.

When liquid medications are administered using methods such as oral medication administration (i.e., swallowing the medication) or receiving the medication via a needle-based injection or a drip line, the amount of medication being dispensed is typically easily controllable and verifiable using simple measuring and/or viewing techniques. However, when the fluid is delivered to the patient internally through a tubular device, the ability to observe and adjust the medication administration can be more difficult. Thus, a number of systems have been developed for delivering therapeutic fluids to treatment sites within a patient that include minimally invasive, tubular delivery lumens (e.g., catheters or endoscopes) and fluid sources that are actuated by a plunger. This plunger can help the user to control the amount of fluid that is delivered to and/or expelled from the system. In some cases, the minimally invasive fluid delivery systems are not reusable, as the cost to sterilize the components can be prohibitive. These systems can include needleless fluid injection systems, for example. Needleless devices and methods for treating tissue of the urinary tract are discussed in Applicants' copending application U.S. Patent Application Publication No. 2006/0129125 and U.S. Ser. No. 12/087,231, filed Jun. 27, 2008 (Copa et al.), titled "Devices, Systems, and Related Methods for Delivery of Fluid to Tissue", the entire disclosures of which are incorporated herein by reference.

Another issue that can be encountered with these fluid delivery systems is that a specific configuration of a system may not be adaptable or adjustable for use with multiple fluids having differing material properties, such as viscosity. In particular, these existing systems can often include long tubular components through which fluid needs to travel, such as one or more elongated lumens or catheters, and fluids with different viscosities can react differently to the resistance and friction encountered when moving through fluid tubular components. Due to this resistance, a fluid with a particular viscosity may exit the distal delivery end of an injection orifice with a significantly different amount of pressure or force than a fluid having a different viscosity when using the same injection pressure. If the exit force of the fluid is too high or low, the fluid administration at the treatment site may be ineffective. In addition, differences in the mechanical features of the system may contribute to or cause reduced or enhanced delivery pressure and/or fluid delivery velocity.

Due to the widely varied system and fluid requirements associated with the delivery of therapeutic compositions to treatment locations in a patient, there is a need to provide improved procedures, systems, and components for fluid delivery. Such procedures, systems, and components would provide for accurate and controlled dispensing of therapeutic compositions to specific treatment locations within a patient, and further would compensate for different fluid properties, such as viscosity.

SUMMARY

The invention generally involves needleless fluid injection devices, systems, and methods. These devices and systems allow for targeted delivery of therapeutic fluids at desired anatomical tissue locations, such as locations in the male or female urinary tract, (e.g., bladder, bladder neck, kidney, ureters, urethra, prostate, etc.). The therapeutic fluids can include biologically active species and agents such as chemical and biochemical agents, for example. Exemplary devices can be designed to deliver fluid at various tissue locations, and can further deliver multiple different therapeutic fluids having varying material properties (e.g., viscosity). The devices IO can be capable of delivering precise amounts of fluid for injection at precise locations and at specific pressures that are adjustable depending on the fluid being administered to the location in the patient.

In one aspect of the invention, a needleless injection system is provided to deliver therapeutic fluids to an internal treatment site in a patient, where the system is pressurized and is capable of compensating for differences in injection media viscosity and mechanical system characteristics.

In another aspect of the invention, a needleless therapeutic fluid injection system is provided, which generally comprises an injection chamber and an applicator lumen. The injection chamber can include one or more sensors that detect the data used to determine the flow rate of an injection fluid or injectate.

These sensors can be located on an injection cylinder of the injection chamber, for example. The sensors can detect a speed at which a plunger of the system moves when the system is being primed or run through a test cycle using a predetermined pressure. Data received from the sensors can then be used by a microprocessor-based control system to calculate the flow rate of the injection fluid, wherein the control system may be located within a console. This flow rate can then be used to calculate the injection pressure required to achieve a specified injection depth and/or velocity for that fluid exiting the system.

In another aspect of the invention, a method is provided for delivering a therapeutic fluid using a needleless fluid delivery system. The method generally comprises providing a needleless fluid delivery system having a minimally invasive access device (e.g., a shaft or catheter tube), an injection chamber, and an injector assembly or console. The method can also include accessing a treatment location with the minimally invasive access device, infusing injection media into the fluid delivery system at a set or predetermined pressure, measuring the flow rate of the fluid with at least one sensor, which may be incorporated into the console or injector assembly, determining the injection pressure based upon the flow rate required to achieve the desired injection depth, and adjusting the injection pressure until the desired injection depth for the fluid exiting the access'device or shaft is achieved.

In another aspect of the invention, the assessment of flow rate will take place before the treatment location is accessed by the device. It is further noted that the injection pressure can then be adjusted after the desired depth is achieved. The pressure will be adjusted based on these measurements to achieve an equivalent scale of user-controlled "injection power" versus fluid or jet speed.

In another aspect of the invention, a method is provided for compensating for variability in a pressurized drug injection system. The method comprises providing a needleless fluid delivery system having a minimally invasive access device (e.g., a shaft or catheter tube), an injection chamber, and an injector assembly or console. The method can also include accessing a treatment location with the minimally invasive access device, infusing injection media into the fluid delivery system at a set injection speed, measuring the pressure with at least one sensor that is incorporated into the console or injector assembly, determining the injection pressure based upon the flow rate required to achieve the desired injection depth, and maintaining the pressure so that the desired injection depth is achieved.

In another aspect of the invention, a needleless therapeutic fluid injection system is provided that includes modular, interchangeable components. In particular, the system can comprise a console that generally includes the electronic and/or pneumatic control components for the system, an injection chamber, and a shaft or catheter tube. The console and injection chamber are functionally attached in such a way that the console can control the pressure that is generated in the injection chamber for fluid administration at the distal end of the shaft or catheter tube. The injection chamber comprises a syringe-type structure, where the movement of a plunger of the syringe is controlled by the console. However, the injection chamber can be disconnected from the console, and the injection chamber and its attached catheter tube can be discarded, if desired. Notably, the fluid contained within the injection chamber does not come in contact with any portion of the console, therefore, the console is reusable for multiple cycles simply by attaching and detaching different injection chambers. Further, the proximal end of the shaft or catheter tube may be either detachably or permanently connected to the injection chamber.

In another embodiment of the invention a test sequence is used to establish the operating parameters for a fluid injection system of the types described herein. In particular, this test sequence can be used to adjust the operating parameters of the system to compensate for different fluid viscosities. The test sequence involves using a reference fluid, such as water, which is provided to the system in the injection chamber. The reference fluid is then pressurized and dispersed from the distal end of the catheter tube. During this process, sensors that determine how fast the fluid moves when subjected to a certain amount of pressure can take one or more measurements. A therapeutic fluid can then be provided to the injection chamber, where it is also pressurized and dispensed from the distal end of the catheter tube, while speed measurements are again taken by the sensors. The measurements can be taken at a relatively low pneumatic pressure and also at a relatively high pneumatic pressure, along with intermediate pressures, if desired, and these measurements are compared to the characteristics of the reference fluid. The console can then be calibrated to compensate for the fluid viscosity of the therapeutic fluid.

In another aspect of the invention, the viscosities of both a reference fluid and a therapeutic fluid are known, such that a method involves testing the system with the reference fluid to characterize the actual device being used, then the device is drained of the reference fluid. The pressure scale is then adjusted based on the performance of the particular device and the viscosity of the therapeutic fluid. At this point, the therapeutic fluid can be loaded and injected. In this way, therapeutic fluid is conserved. In order to interpret the data points of jet speed versus pressure for given device and find the pressure needed for the desired speed, the following equations can be used:

$$v_{jet} = \frac{v_{plunger} A_{inj.cham.bore}}{N_{orifices} A_{jet}} = \frac{Q_{total}}{N_{orifices} A_{jet}}$$

$$v_{jet} \propto \sqrt{P_{injection}}$$

To more generally determine the pressure where only the viscosity is known and no calibration test is preformed, the Darcy-Weisbach Equation can be used in conjunction with Bernoulli's Equation.

BRIEF DESCRIPTION OF THE DRAWINGS

The present invention will be further explained with reference to the appended Figures, wherein like structure is referred to by like numerals throughout the several views, and wherein.

DETAILED DESCRIPTION

The invention relates to devices and methods useful for injecting fluid into tissue for treatment. The fluid can be injected without the use of a needle and can therefore be referred to as a needleless fluid injection system. Needleless fluid injection systems of the invention can include one or more orifices that deliver fluid in the form of a stream of fluid, which may be referred to as a jet or fluid stream, at a pressure, velocity, and stream size that allow the fluid stream to pass through a tissue surface, penetrate into the bulk of the tissue below the tissue surface, and become dispersed as fluid particles within the tissue, such as in the form of a cloud of dispersed fluid particles or droplets, without a needle structure passing into the tissue. The type of tissue injected for treatment can be any amenable tissue, which can include tissue at or near the urinary tract (e.g., tissue of the prostate, kidneys, ureters, urethral tissue, bladder (including the bladder neck), etc.), or other tissues such as heart tissue, as desired.

Needleless devices of the type described herein generally include a distal end and a proximal end. As used herein, a "distal end" of a device or system refers to an end area or portion of the device or system that can be introduced internally within a patient's body during a treatment procedure. For example, an elongate shaft or catheter of the needleless injection systems of the invention generally include a distal end that is the first portion of the device that is introduced into the patient for treatment. A distal end may include functional features that operate on fluid or tissue during use, such as one or more ejection orifices, delivery heads (e.g., end effectors, nozzles, etc.) that house one or more ejection orifices, a frictional tissue holding tip, tissue tensioners, lighting or other optical features, steering features, and the like.

As used herein, a "proximal end" of an exemplary needleless device or system is the end that is opposite the distal end of that device or system. To that end, each component of a system can include its own proximal and distal ends, while the overall system can also include proximal and distal ends. For one example, a needleless fluid injection system of the invention can include an injector body or console at a proximal end that remains external to the patient during use and an elongate shaft or catheter tube at a distal end. That is, exemplary needleless fluid delivery devices or systems can include a proximal end that includes a console, and an elongate shaft extending from a proximal end, which is in communication with the console, to a distal end. One or more injection orifices at the distal end can be in fluid communication with the console.

An exemplary console used with systems of the invention can include a housing that connects to or is otherwise (directly or indirectly) in fluid communication with an elongate shaft. The console can include fluid that can be pressurized by a pressure source to cause the fluid to flow through the shaft for injection into tissue at the distal end. A device can eject fluid from one or multiple ejection orifices that can be located at the distal end of the shaft.

Devices, systems, and methods are described herein that can be used to inject a fluid through a surface of a tissue, without the use of a needle penetrating through the tissue surface and into the bulk of the tissue, and dispersing as particles or droplets within the tissue below the tissue surface. The injected fluids may be referred to as an "injectate" or "injection fluid", which may be any type of fluid such as a therapeutic fluid. The injectate can be administered into tissue in a needleless manner, whereby the injectate is delivered as a pressurized fluid stream or jet. This contrasts with injections performed using a needle, whereby a hollow needle structure penetrates tissue to locate a hollow end of the needle within a tissue mass, below the tissue surface, after which the needle carries fluid into the bulk of the tissue and delivers the fluid at a relatively low pressure to the tissue in the form of a body or pool of fluid known as a bolus.

Figure 1:
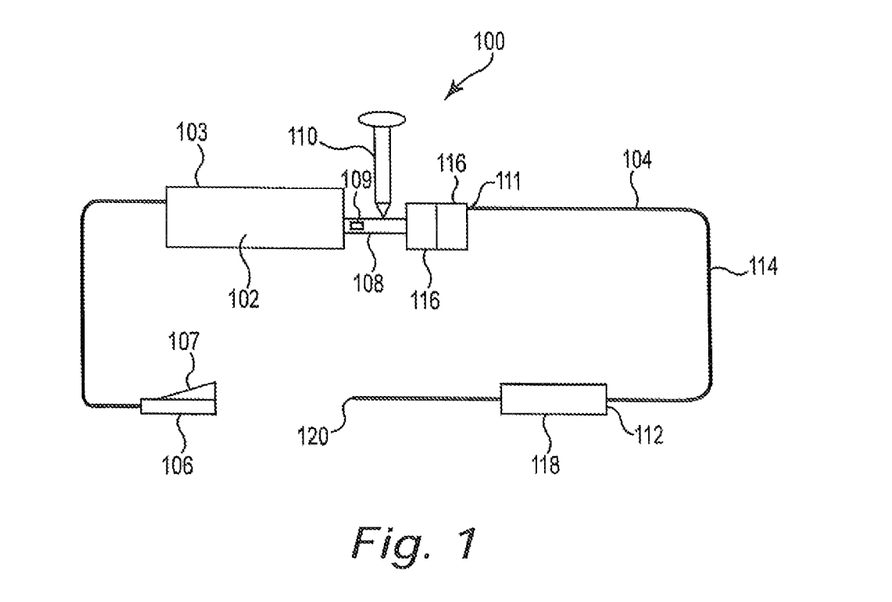
FIG. 1 is a schematic illustration of one embodiment of a needleless fluid delivery system for delivering a therapeutic fluid to a treatment location, in accordance with the invention.

Referring now to the Figures, wherein the components are labeled with like numerals throughout the several Figures, and initially to FIG. 1, one preferred configuration of a needleless fluid delivery system 100 is illustrated. Delivery system 100 generally includes an injection console or console 102, an injection chamber 108, and a catheter tube or elongate shaft 104. The console 102 includes a user interface 106, which can be used for activating and controlling the activities of the various components of the delivery system 100. The user interface 106 can include an input means for selectively delivering a pressurized fluid through the injection chamber 108. The user interface 106 may further include one or more actuatable devices, such as a foot petal 107 (as shown), a hand activated controller, switches, buttons, and/or the like. It is also contemplated that the user interface 106 can include a touch-screen that is capable of receiving touch commands and may optionally include a display system for displaying information such as the mode of operation that is being used and/or certain operating parameters of the system.

Although console 108 can include a wide variety of features, any console used in the fluid delivery systems of the invention can generally include a housing, a pressure chamber, and a pressure source. A console can have any configuration, size, or design, ranging from a small, handheld design to a relatively larger floor or table-mounted console. The consoles can also include separate or separable components such as a pressure chamber or injection chamber that can be attached, used for an injection procedure, and detached and optionally discarded or sterilized and reused. A shaft or catheter tube can also be attached to a console or a pressure chamber in a manner that facilitates separation and optional re-attachment or disposal. With separable components, a shaft or injection chamber can be attached to a console housing and used to inject a first patient and/or a first injectate, and then the shaft or pressure chamber can be removed and discarded or sterilized. A second shaft or pressure chamber can then be attached to the console to treat a second patient or the first patient with second injectate or administer another treatment of the first injectate. The second patient or injectate can involve injection and treatment of the same type of tissue as the first patient or injectate, or of a new type of tissue than was treated in the first treatment. In this manner, separable and optionally disposable shaft or pressure chamber components of a needleless injection system can allow a console housing to be used multiple times to inject the same or different injectates to the same or different patients, and to the same or different types of body tissue, thereby providing an injection system that is flexible for use in a wide variety of situations and with a wide variety of fluids.

A console can further include actuating features to control distal end features of the system, such as for steering a steerable distal end of a steerable shaft or catheter tube or to actuate ejection of fluid (control fluid or injection fluid). A console can further include actuating features to move a moveable or extendable injection shaft or one or more injection orifices or control orifices relative to another shaft component such as a working shaft. A console can further include optional ports to connect a console housing to auxiliary devices, electronics (e.g., control systems), and optical features such as a lens, fiber optic, or electronic viewing mechanism. One or more attachment ports can optionally attach a console to an external and optionally remote component such as an external or remote pressure source, vacuum source, or an external or remote fluid reservoir to supply injectate or control fluid. For example, a console housing may have a fluid port that attaches to a source of a fluid (e.g., injectate or control fluid), to supply the fluid to the console housing, such as to a permanent or detachable pressure chamber. The console can include a pressure chamber and a pressure source capable of pressurizing a fluid contained in the pressure chamber to cause the fluid to flow from the console, through a lumen in the shaft, and then through an ejection orifice as either injectate or a control fluid.

In embodiments of devices that involve the use of a control fluid, a pressurized control fluid can be produced by a console using any useful technique and mechanism. For example, the pressurized control fluid can be produced by a pressure source, such as any pressurized fluid source, magnetohydrodynamic power, expanding steam or gas power, or the like, with any available and useful control fluid, which may be a liquid or a gas.

The injection chamber 108 can include a surface opening 109, which can provide an opening through which a sensor can detect a plunger or detect when it has reached a certain point (e.g., to gauge its speed), for example, and a therapeutic fluid supply 110. Fluid supply 110 can be provided as a syringe that is manually activated, such as by physically pressing a plunger into a syringe barrel that is at least partially filled with fluid to push fluid from the syringe barrel. Alternatively, fluid supply 110 can be automatically or mechanically activated, such as with an electronic fluid supply controller or with one or more remote activation devices that can be manipulated by the user to move the plunger into and out of a syringe barrel. In yet another alternative, the fluid supply 110 is not a syringe, but instead includes a larger fluid source, such as a reservoir or other container that holds the fluid until it is provided to the injection chamber 108. Such a container can be positioned so that the fluid is gravity fed to the injection chamber, for example, or so that the fluid can be extracted using a vacuum source, for another example. With any of the different types of fluid supplies used with the systems of the invention, it is contemplated that an exact amount of fluid to be administered can be premeasured and provided to the system until that quantity of fluid is depleted and/or a predetermined amount of fluid can be extracted from a relatively large fluid supply.

A fluid chamber can be a space or volume at a proximal end of a device, such as at a console housing, that can be used to contain pressurized or non-pressurized fluid (e.g., control fluid or injectate). Examples of specific types of fluid chambers include fluid reservoirs and pressure chambers. Optionally, a proximal end of a device may include one or multiple fluid reservoirs and pressure chambers, which can be provided for one or more different fluids including one or more injectates, one or more control fluids, or combinations of injectates and control fluids.

A fluid reservoir is generally a type of fluid chamber that can contain a fluid for a purpose of containing, transferring, holding, or storing a fluid, such as a fixed volume fluid chamber, and may be included as a permanent or removable (i.e., attachable and detachable) component of a console housing.

A pressure chamber or injection chamber can be a type of fluid chamber for containing one or more fluids (e.g., control fluid or injectate) for a purpose of placing the fluid under pressure to deliver the fluid through a lumen to a distal end of a shaft for ejection from an ejection orifice. Examples of pressure chambers include a syringe chamber and other variable volume spaces that can be used to contain and pressurize a fluid. Examples of variable volume pressure chambers include spaces that can exhibit a variable volume for increasing or decreasing the volume (and correspondingly decreasing or increasing pressure) within the variable volume chamber space. Such pressure chambers can include a plunger, piston, bellows, or other mechanisms. A pressure chamber can be pressurized by a pressure source attached to the plunger, bellows, or piston, etc., such that fluid contained in the pressure chamber is ejected under pressure. This pressurized fluid can be used for priming a device and/or for ejecting fluid from an ejection orifice for injection and/or to produce a control force, for example. A pressure source may be any source of energy (e.g., mechanical, electrical, hydraulically derived, pneumatically derived, or the like) such as a spring, solenoid, compressed air, manual syringe, electric power, hydraulic, pneumatic pressure sources, or the like. A pressure chamber may be a permanent or removable (i.e., attachable and detachable) component of a console housing.

Referring again to FIG. 1, a proximal or supply end 111 of the catheter tube or shaft 104 extends from a distal end of the injection chamber 108. The catheter tube 104 may be permanently attached or connected to the injection chamber 108 so that the tube 104 and chamber 108 are provided to the system either as a single component. Alternatively, catheter tube 104 may be attachable and detachable from injection chamber 108, such as with quick connection fittings, so that the injection chamber 108 and tube 104 are provided to the system as separate components. Catheter tube 104 further includes a delivery or distal end 112, which is generally opposite the proximal or supply end 111.

Catheter tube or shaft 104 is a generally continuous, elongated tube, which may include multiple lumens, attachments, or other components that may extend along all or part of the length of the tube 104. Catheter tube 104 may further comprise a number of different configurations, such as an endoscope or other catheter configuration, for example. Alternatively, catheter tube 104 can comprise a flexible tube 114 to allow for easy positioning of the delivery or distal end 112 within the patient. Supply or proximal end 111 of the tube 104 can be generally configured to attach to the injection chamber 108 and can include a quick-connect style connector, which is schematically illustrated as connector 116. One example of a type of connection that can be used includes compression fittings, although any type of connector can be used that provides a secure engagement between components.

Delivery or distal end 112 can comprise a number of different configurations, which can be selected to provide treatment to a certain location in the patient's body (e.g., a rectal treatment location, a gastrointestinal treatment location, a nasal treatment location, a bronchial treatment location, or an esophageal treatment location). The configuration of this distal end 112 is designed and/or selected to provide different types of treatment, such as can be provided by end-fire applicators or side-fire applicators. Further, in some embodiments, the catheter tube 104 can include an application specific applicator, such as applicator 118, which in turn includes a fluid administration port 120.

Examples of injection shaft configurations, features and combinations of shaft features that can be useful according to the present description are identified as U.S. Patent Application Publication No. 2006/0129125 and U.S. Ser. No. 12/087,231, filed Jun. 27, 2008 (Copa et al.), titled "Devices, Systems, and Related Methods for Delivery of Fluid to Tissue"; and in Assignee's copending patent application titled "Devices, Systems, and Related Methods for Delivery of Fluid to Tissue", by Crank, filed on Dec. 4, 2009, PCT Patent Publication No. WO 2010/065133; and in Assignee's copending patent application titled "Needleless Injection Device Components, Systems, and Methods", by Crank, filed on Dec. 4, 2009, PCT Patent Publication No. WO 2010/074705, which are all incorporated herein by reference.

In another aspect of the invention, in communication with a proximal end of a device is an elongate shaft that extends from the proximal end (i.e., from a proximal shaft end), that is optionally removably connected to the console (or a component of the console such as a removable pressure chamber), to a distal end that can be placed in a patient during an injection procedure. A shaft can be of various designs, minimally including an injection lumen to carry injectate from a proximal end of the device to a distal end of the shaft. A useful shaft may optionally include at least one separate lumen for carrying control fluid to a distal end.

An injection shaft minimally includes an injection lumen in communication with an injection orifice. The injection shaft can include structure such as sidewalls that define the injection lumen, the sidewalls being of sufficient strength to withstand operating pressures used to deliver injectate from the injection orifice at an elevated pressure sufficient to cause the injectate to be ejected from the injection orifice to penetrate a tissue surface and become injected and into and dispersed below the tissue surface. An injection shaft may be constructed of a flexible material (e.g., a metal or polymeric tube) and may be prepared from exemplary materials capable of withstanding pressure of an injection, e.g., nitinol, stainless steel, reinforced (e.g., braided) polymer.

A basic version of an injection shaft of a device as described can be an "injection shaft" that includes a proximal end, a distal end, and a sidewall that defines an internal lumen ("injection lumen"), and at least one injection orifice at the distal end in connection with the injection lumen. An injection shaft can optionally include multiple injection orifices, optionally one or more control orifices at the distal end, and optionally a control lumen extending from the proximal end to the optional control orifice.

An injection shaft can be any elongate structure capable of delivering fluid to a distal end of a shaft at a pressure suitable to inject tissue, as described. Exemplary injection shaft structures include relatively flexible hollow bodies having a distal end, a proximal end, sidewalls extending between the ends, an internal lumen ("injection lumen") defined by interior surfaces of the sidewall. The injection lumen is in communication with one or more injection orifices at the distal end. The injection orifices may include a member of different configurations, such as an aperture or bore in an injection shaft sidewall, an aperture or bore in a nozzle, end effector, injection head, or other structure in communication with the injection lumen.

Figure 2:
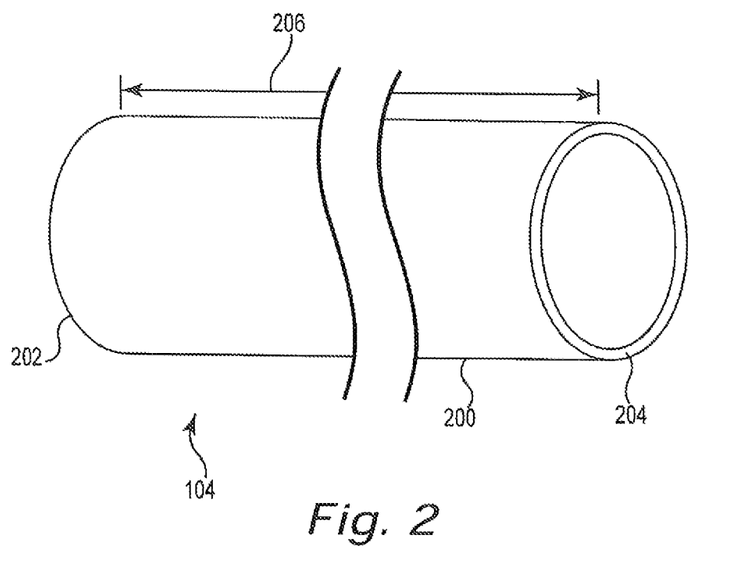
FIG. 2 is a side view of an embodiment of a tube-like device of the invention, which may be a non-metal, polymeric tube component.

Referring now to FIG. 2, a portion of one exemplary cathether tube 104 is illustrated, which can include a non-metal, polymeric tube material 200 that has a proximal attachment end 202 and a distal treatment end 204. Tube 200 has a tube length 206 that corresponds generally to the type of treatment being performed on the patient. In other words, the tube length 206 is chosen to correspond with the location of the body to which the distal treatment 204 needs to be positioned and the type of treatment being performed to treat a particular area of the body. For example, when the device 200 is configured for use for performing a cytoscopic or endoscopic procedure, the tube length 206 can range from about 18 inches to about 72 inches in length, although it is contemplated that the tube 104 can be longer or shorter than this range. The tube 200 may be made of a wide variety of materials and combinations of materials, such as NiTi, Polyetheretherketone (PEEK), PEI, PI, braided polymers, stainless steel, and the like.

When fluid flows through the inner portion of the catheter tube 104 for a treatment procedure, it will be subjected to a certain amount of resistance caused by its contact with the inner walls of tube 104. The amount of resistance will be greater for relatively long tube lengths and relatively small tube inner diameters, and should be taken into consideration when calculating or determining the desired characteristics that the fluid will have when it reaches the distal or delivery end of the tube. In addition, the amount of resistance will further be impacted by the fluid chosen to be administered by the system 100. In particular, the fluid viscosity correlates to the amount of resistance that is experienced by the fluid. In addition, various mechanical characteristics of an injection system may affect the pressure of fluid flowing through the system, such as surface roughness, mechanical obstructions to straight fluid flow (e.g., elbows or bends in the fluid path), and/or other obstructions to fluid flow.

Figure 3:
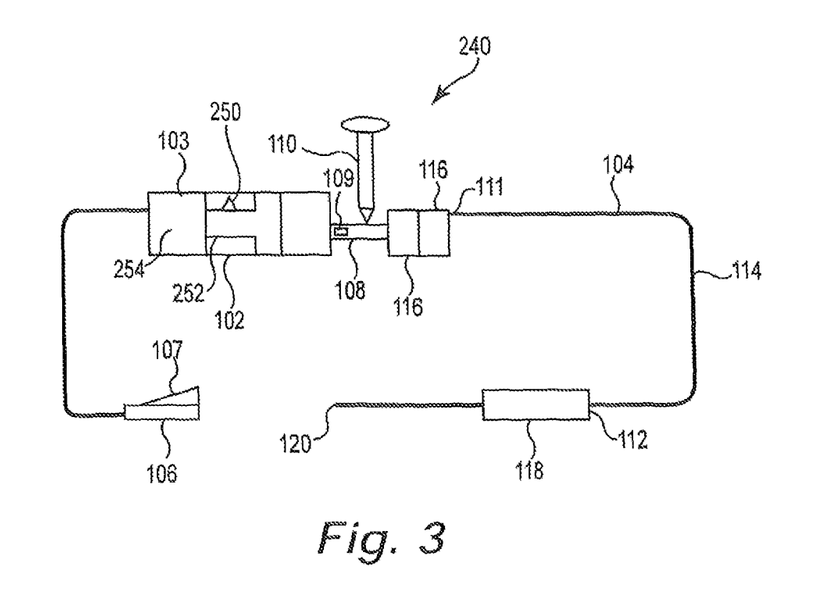
FIG. 3 is a schematic illustration of an embodiment of a needleless fluid delivery system of the invention, which is capable of adjusting injection properties in response to certain fluid properties that are exhibited when delivering a therapeutic fluid to a treatment location of a patient.

To account for these differences in the injection systems and injection fluids, a needleless fluid delivery system 240 of the type illustrated in FIG. 3 can be used. This system 240 includes one or more sensors 250 that are used for detecting data and to determine the flow rate of the injection media being used. The sensors may include, for example, pressure sensors, strain gauges, optical sensors, Hall Effect sensors, magnetic sensors, linear voltage displacement transducers, inductance transducers, capacitance sensors, and/or the like. The sensors 250 can be located on an injection cylinder 252 of the injection chamber 108, for example. The sensors 250 can detect the speed of the plunger during a test cycle for the needleless fluid delivery system 240. This plunger speed is measured at a set or constant predetermined pressure. Plunger speed data obtained by the sensors 250 is used by a computer control system for an injector 103 of the injector console 102 to calculate the flow rate. This flow rate is then used to calculate the injection pressure required to achieve a specific injection depth for the fluid at the distal end of the catheter tube. Using the sensors in this way can reduce the variability in injection depths achieved when using different fluids with certain pressurized injection systems.

In accordance with the invention, a method of compensating for system variability and injection media variability in a pressurized drug injection system is provided. This method includes the step of providing a needleless fluid delivery system that includes a minimally invasive access device, such as an elongated shaft or catheter tube, an injection chamber, and a console. The method also includes the step of accessing a treatment location with the minimally invasive access device, infusing injection fluid into the fluid delivery system at a set pressure, measuring the flow rate with at least one sensor that is incorporated into the injection assembly, determining the injection pressure based upon the flow rate that is required to achieve a desired depth of injection at the distal end of the device, and adjusting the pressure until the desired depth of injection is achieved. In one embodiment, the injection pressure versus speed calibration is performed before accessing the treatment area.

Figure 4:
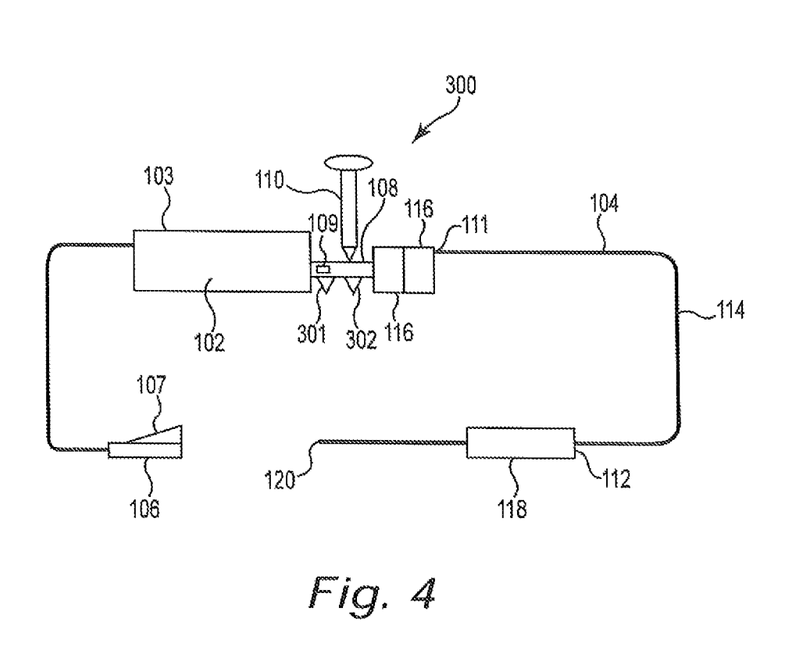
FIG. 4 is a schematic illustration of an embodiment of a needleless fluid delivery system of the invention, which is capable of adjusting injection properties in response to certain fluid properties that are exhibited when delivering a therapeutic fluid to a treatment location of a patient.

Another embodiment of the invention includes a needleless injection system 300, as is illustrated in FIG. 4. This system 300 includes a first sensor 301 that is positioned on the injection chamber 108 and used to detect a pressure, and a second component 302 that is also positioned on the injection chamber 108 and is used for delivering fluid at a set injection speed. Rather than measuring the flow rate via the plunger speed at a set injection pressure, this injection system 300 is used to determine the flow characteristics of a particular fluid by measuring the pressure at a set injection speed. In this way, the system is capable of compensating for variability in a pressurized drug injection system. The method used includes the steps of providing a needleless fluid delivery system having a minimally invasive access device or catheter tube, an injection chamber, and an injector console. The method further includes the steps of accessing a treatment location with the minimally invasive access device, infusing injection media into the fluid delivery system at a set injection speed, measuring the pressure with at least one sensor that is incorporated into the injection device, determining the pressure of the fluid based upon the flow rate required to achieve the desired injection depth, and maintaining the pressure so that the desired depth of fluid injection can be achieved.

In another embodiment of the invention, a test sequence is used to establish the operating parameters for a fluid injection system of the types described herein. In particular, this test sequence can be used to adjust the operating parameters of the system to compensate for different fluid viscosities. The test sequence involves using a reference fluid, such as water, which is provided to the system in the injection chamber. The reference fluid is then pressurized and dispersed or administered from the distal end of the catheter tube. During this process, measurements are taken by sensors that determine how fast the fluid is moving when subjected to a certain amount of pressure. A test portion of a particular therapeutic fluid can then be provided to the injection chamber, where it is also pressurized and dispensed from the distal end of the catheter tube, while speed measurements are taken by the sensors. The measurements can be taken at a relatively low pneumatic pressure and also at a relatively high pneumatic pressure, along with intermediate pressures, if desired, and these measurements are compared to the characteristics of the reference fluid. The console can then be calibrated to compensate for the fluid viscosity of the therapeutic fluid. As set out above, however, in one aspect of the invention, the assessment of flow rate will take place before the treatment location is accessed by the device, etc. In yet another embodiment of the invention, the delivery system includes an injection console and a catheter tube, along with a manually activated syringe.

The needleless therapeutic fluid delivery systems of the invention can be used by medical professionals in combination with a medical imaging system such as a computer axial tomography (CAT) system, a magnetic resonance imaging (MRI) system, or a transrectal ultrasound (TRUS) system (used in the case of treating a prostate gland), for example. Through the use of such a medical imaging system, the medical professional can verify the location of the delivery or distal end of the system for proper insertion thereof relative to the desired treatment location.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the Invention. Thus, the scope of the present invention should not be limited to the structures described herein, but only by the structures described by the language of the claims and the equivalents of those structures.

The invention claimed is:

1. A method of determining a flow rate of a fluid in a needleless injection system, wherein the system comprises:
   a console comprising control components for the injection system;
   an injection chamber operatively connected to the console and comprising an injection cylinder and at least a first sensor,
   a plunger positioned for slideable movement within the injection cylinder; and
   an injection shaft operatively connected to the injection chamber, the injection shaft comprising a distal end and at least one injection orifice at the distal end for delivering a first fluid and a second fluid at a pressure, velocity, and stream size that corresponds to its viscosity for passing through a tissue surface, penetrating into tissue below the tissue surface, and dispersing fluid particles within the tissue, the method comprising the steps of:
   providing the first fluid to the injection chamber;
   pressurizing the first fluid to a first pressure;
   moving the plunger relative to the injection chamber and evacuating at least a portion of the first fluid from the injection chamber while detecting a first speed of the plunger with the first sensor;
   providing the first speed of the plunger detected by the first sensor to the console;
   calculating the flow rate of the first fluid; and
   controlling pressure generated in the injection chamber by the console for fluid administration of at least one of the first and second fluids from the injection orifice at the distal end of the injection shaft at an injection speed that corresponds to a viscosity of at least one of the first and second fluids.

2. The method of claim 1, further comprising the steps of:
   using the flow rate of the first fluid to calculate an injection pressure required to achieve a predetermined velocity for the second fluid.

3. The method of claim 2, wherein the first fluid has a different viscosity than a viscosity of the second fluid.

4. The method of claim 2, wherein the first fluid comprises at least one material property that is different from that material property of the second fluid.

5. The method of claim 1, further comprising the steps of:
   providing the second fluid to the injection chamber;
   pressurizing the second fluid to a second pressure;
   moving the plunger relative to the injection chamber and evacuating at least a portion of the second fluid from the injection chamber while detecting a second speed of the plunger with the first sensor;
   providing the second speed of the plunger detected by the first sensor to the console; and
   calculating the flow rate of the second fluid.

6. The method of claim 5, further comprising the step of comparing the flow rate of the first fluid to the flow rate of the second fluid.

7. A needleless injection system comprising:
   a console comprising control components for the system;
   an injection chamber removeably attached to the console and comprising at least a first speed sensor for detecting fluid speed; and
   a first injection shaft attached at a proximal end to the injection chamber for fluid communication with an injection cylinder of the injection chamber;

wherein the console controls the pressure that is generated in the injection chamber for fluid administration at a distal end of the injection shaft;

wherein the injection chamber further comprises a plunger that is moveable within the injection cylinder in response to pressure changes within the injection cylinder; and wherein pressure generated in the injection chamber is controllable by the console for administration of fluids from a distal end of the injection shaft at an injection speed that corresponds to viscosities of the respective fluids as determined by the console.

8. The needleless injection system of claim 7, further comprising a quantity of fluid within the injection chamber, wherein the fluid within the injection chamber is isolated from the control components of the console.

9. The injection system of claim 7, wherein the first injection shaft is removeably attached to the injection chamber.

10. The injection system of claim 9 in combination with at least a second injection shaft that is removeably attachable to the injection chamber after detaching the first injection shaft.

11. The injection system of claim 10, wherein the first and second injection shafts comprise different distal end features.

* * * * *